(12) United States Patent
Meyer et al.

(10) Patent No.: US 8,286,488 B2
(45) Date of Patent: Oct. 16, 2012

(54) APPARATUS AND SYSTEM FOR MEASURING MATERIAL THICKNESS

(75) Inventors: Paul Meyer, McVeytown, PA (US); Jeffrey Anderson, Lewistown, PA (US); Anand Desai, Lewistown, PA (US); Wei Luo, Boalsburg, PA (US)

(73) Assignee: General Electric Company, Schenectady, NY (US)

( * ) Notice: Subject to any disclaimer, the term of this patent is extended or adjusted under 35 U.S.C. 154(b) by 561 days.

(21) Appl. No.: 12/434,357

(22) Filed: May 1, 2009

(65) Prior Publication Data
US 2010/0275692 A1 Nov. 4, 2010

(51) Int. Cl.
*G01B 17/02* (2006.01)
(52) U.S. Cl. ............... 73/600; 73/609; 73/614; 73/615
(58) Field of Classification Search ............... 73/570, 73/584, 600, 606, 609, 614, 615, 649
See application file for complete search history.

(56) References Cited

U.S. PATENT DOCUMENTS

| | | | |
|---|---|---|---|
| 2,784,325 A * | 3/1957 | Jefferys et al. ............ 310/336 |
| 3,646,805 A * | 3/1972 | Walters ...................... 73/611 |
| 3,665,754 A | 5/1972 | Krautkramer et al. |
| 3,918,296 A * | 11/1975 | Kitada ........................ 73/627 |
| 3,942,358 A * | 3/1976 | Pies ........................... 73/611 |
| 3,960,005 A * | 6/1976 | Vezina ........................ 73/614 |
| 4,088,028 A * | 5/1978 | Hildebrandt ................ 73/611 |
| 4,182,155 A * | 1/1980 | Fowler ....................... 73/1.81 |
| 4,398,421 A * | 8/1983 | White ......................... 73/597 |
| 4,545,248 A * | 10/1985 | Kitada et al. ............... 73/597 |
| 4,567,770 A * | 2/1986 | Rumbold et al. ........... 73/644 |
| 4,570,486 A * | 2/1986 | Volkmann ................... 73/597 |
| 4,712,428 A * | 12/1987 | Ishii et al. .................. 73/644 |
| 5,932,807 A | 8/1999 | Mallart |
| 5,951,908 A * | 9/1999 | Cui et al. ................ 252/62.9 R |
| 6,035,717 A * | 3/2000 | Carodiskey ................. 73/597 |
| 6,070,466 A * | 6/2000 | Taran et al. ................. 73/622 |
| 6,278,224 B1 * | 8/2001 | Sawada et al. ............. 310/334 |
| 6,396,262 B2 | 5/2002 | Light et al. |
| 6,405,596 B1 * | 6/2002 | Kruzic ........................ 73/611 |

(Continued)

FOREIGN PATENT DOCUMENTS
SU 715938 A * 2/1980
(Continued)

OTHER PUBLICATIONS

PCT/US2010/030106, Search Report and Written Opinion, Jul. 2, 2010.

*Primary Examiner* — David Rogers
(74) *Attorney, Agent, or Firm* — Global Patent Operation; Mark A. Conklin

(57) ABSTRACT

An apparatus and system for measuring material thickness of a test object. In one embodiment, the apparatus can include a measurement probe that can have a plurality of transducer elements that can include transmitter elements and receiver elements arranged, respectively, in on a first side and a second side of a gap. The first side and the second side can form a scan area with at least one active group that can have at least one transmitter element and at least one receiver element, which can be separated from the transmitter element in a spaced relationship.

5 Claims, 7 Drawing Sheets

U.S. PATENT DOCUMENTS

| | | | |
|---|---|---|---|
| 6,915,696 B2* | 7/2005 | Dufait et al. | 73/626 |
| 7,328,619 B2 | 2/2008 | Moles et al. | |
| 7,354,556 B2* | 4/2008 | Perkins | 422/128 |
| 7,415,880 B2* | 8/2008 | Renzel | 73/597 |
| 7,428,842 B2 | 9/2008 | Fair et al. | |
| 7,628,075 B2* | 12/2009 | Kennedy et al. | 73/628 |
| 7,757,558 B2* | 7/2010 | Bossi et al. | 73/609 |
| 7,886,605 B2* | 2/2011 | Malin et al. | 73/644 |
| 7,950,284 B2* | 5/2011 | Dijkstra et al. | 73/623 |
| 2002/0050169 A1* | 5/2002 | Ritter et al. | 73/606 |
| 2005/0215901 A1* | 9/2005 | Anderson et al. | 600/445 |
| 2008/0134793 A1* | 6/2008 | Woychik et al. | 73/649 |
| 2008/0314153 A1* | 12/2008 | Langlois et al. | 73/606 |
| 2009/0019937 A1 | 1/2009 | Deemer et al. | |

FOREIGN PATENT DOCUMENTS

| | | |
|---|---|---|
| WO | 01/53009 A1 | 7/2001 |
| WO | 2007128139 | 11/2007 |
| WO | 2008010712 | 1/2008 |

\* cited by examiner

Detail A

B - B

C - C

APPARATUS AND SYSTEM FOR MEASURING MATERIAL THICKNESS

BACKGROUND OF THE INVENTION

This invention relates generally to ultrasonic probes, and more particularly to dual phased array ultrasonic probes that measure the thickness of materials.

Ultrasonic testing is a type of non-destructive testing that is used to inspect test object in order to identify and/or characterize defects, flaws, and other anomalies in the test object. Testing equipment that is used in ultrasonic testing generally includes a probe that sends and receives signals, a test instrument that operates the probe, and a cable that transmits information between the probe and the test instrument.

The probe incorporates transducer elements that are constructed of piezoelectric materials that are responsive to certain stimuli in a manner conducive to non-destructive testing. For example, certain transducer elements that are found in the probes generate acoustic waves in response to electrical waveform pulses that are applied to electrodes connected to the element. These elements are also responsive to acoustic waves, such as those acoustic waves that are reflected from the test object. This generates a voltage difference across electrodes that are connected to the element. For purposes of ultrasonic testing, transducer elements are used to transmit acoustic waves into the test object, transducer elements are used to capture the reflection of those acoustic waves, and the resultant voltage differences caused by the reflected waves are processed in order to analyze the test object.

While many probes utilize the same transducer elements to transmit and to receive the acoustic waves, such probes are typically not suited to measure the thickness of materials that are corroded because of the noise, e.g., the backscattered noise, which is generated by the corrosion. Instead, probes that are used to measure the thickness of corroded materials typically have a pair of transducer elements, one that transmits the acoustic wave to the test object, and one that receives the reflected acoustic waves from the test object. Probes that are of the type suited to measure the thickness of corroded materials, however, are not often compatible with test objects that have large surface areas.

One reason for this is because the field of view of these probes is much smaller than the area of interest of the test object. This makes testing large areas of interest highly inefficient, and in many cases very costly. Moreover, because the ratio of the field of view of the probe to the area of interest of the test object is small, the likelihood increases that defects in the area of interest will be missed because the defects may not fall within the field of view of the probe.

Therefore, it would be advantageous to have an apparatus that can provide highly accurate measurement of material thickness for large areas of interest. It would also be advantageous to have an apparatus that can measure the thickness of corroded materials, while being configured in a manner so as to improve the inspection of test objects by reducing both the inspection costs, and the likelihood that defects are missed during the inspection.

BRIEF DESCRIPTION OF THE INVENTION

In one embodiment, a measurement probe for measuring a thickness of a test object, the measurement probe comprising a delay block including a body having a longitudinal axis, the body including a scan surface to be placed proximate the test object, and a support surface opposite the scan surface. The measurement probe also comprising a plurality of transducer elements acoustically coupled to the support surface in a manner forming an active group, the active group including a transmitter side for generating an ultrasound beam, and a receiver side for receiving an echo signal, the receiver side in a spaced relationship with the transmitter side, the spaced relationship forming a gap extending along the longitudinal axis. The measurement probe further comprising and a cross-talk barrier disposed in the gap in a manner acoustically separating the transmitter side from and the receiver side of the active group, wherein the receiver side includes at least one transducer element responsive to the echo signal that corresponds to the ultrasound beam that is directed into the test object from at least one transducer element on the transmitter side.

In another embodiment, a measurement system for measuring a thickness of a material, the system comprising a measurement probe including a delay block having a longitudinal axis and a plurality of transducer elements acoustically coupled to the delay block in a manner forming an active group, the active group including a transmitter side for generating an ultrasound beam, and a receiver side for receiving an echo signal, the receiver side in a spaced relationship with the transmitter side, the spaced relationship forming a gap about the longitudinal axis, the gap including a cross-talk barrier disposed in a manner acoustically separating the transmitter side and the receiver side. The system also comprising a test instrument coupled to the measurement probe, the test instrument including an interface controlling at least one transducer element in the active group in a manner causing a first parameter of the ultrasound beam, wherein the receiver side includes at least one transducer element responsive to the echo that corresponds to the ultrasound beam.

In still another embodiment, a method of imaging a test object with a measurement probe having a delay block including a body having a longitudinal axis, the body including a scan surface to be placed proximate the test object, and a support surface opposite the scan surface. The method comprises forming a plurality of active groups on the support surface with a plurality of transducer elements, each of the active groups including a transmitter side for generating an ultrasound beam, and a receiver side for receiving an echo signal, the receiver side in a spaced relationship with the transmitter side, the spaced relationship forming a gap extending along the longitudinal axis. The method also comprises activating a first active group in a manner generating a first ultrasound beam from a first transducer on the transmitter side of the first active group. The method further comprises receiving the echo signal from the first ultrasound beam with at least one transducer element on the receiver side of the first active group.

BRIEF DESCRIPTION OF THE DRAWINGS

So that the manner in which the above recited features of the present invention can be understood in detail, a more particular description of the invention briefly summarized above, may be had by reference to the embodiments, some of which are illustrated in the accompanying drawings. It is to be noted, however, that the appended drawings illustrate only typical embodiments of this invention and are therefore not to be considered limiting of its scope, for the invention may admit to other equally effective embodiments. The drawings are not necessarily to scale, emphasis generally being placed upon illustrating the principles of certain embodiments of invention. Thus, for further understanding of the nature and objects of the invention, references can be made to the following detailed description, read in connection with the drawings in which.

DETAILED DESCRIPTION OF THE INVENTION

Figure 1:
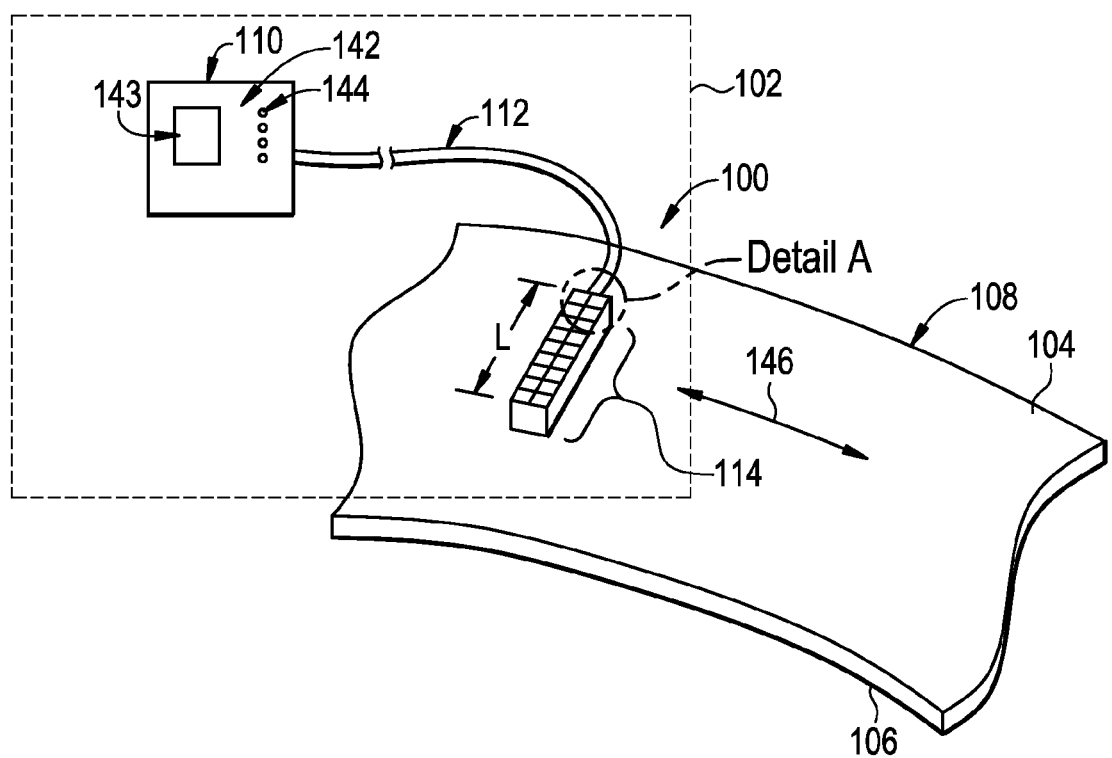
FIG. 1 is a perspective view of a measurement system that includes one embodiment of a measurement probe.
Figure 2:
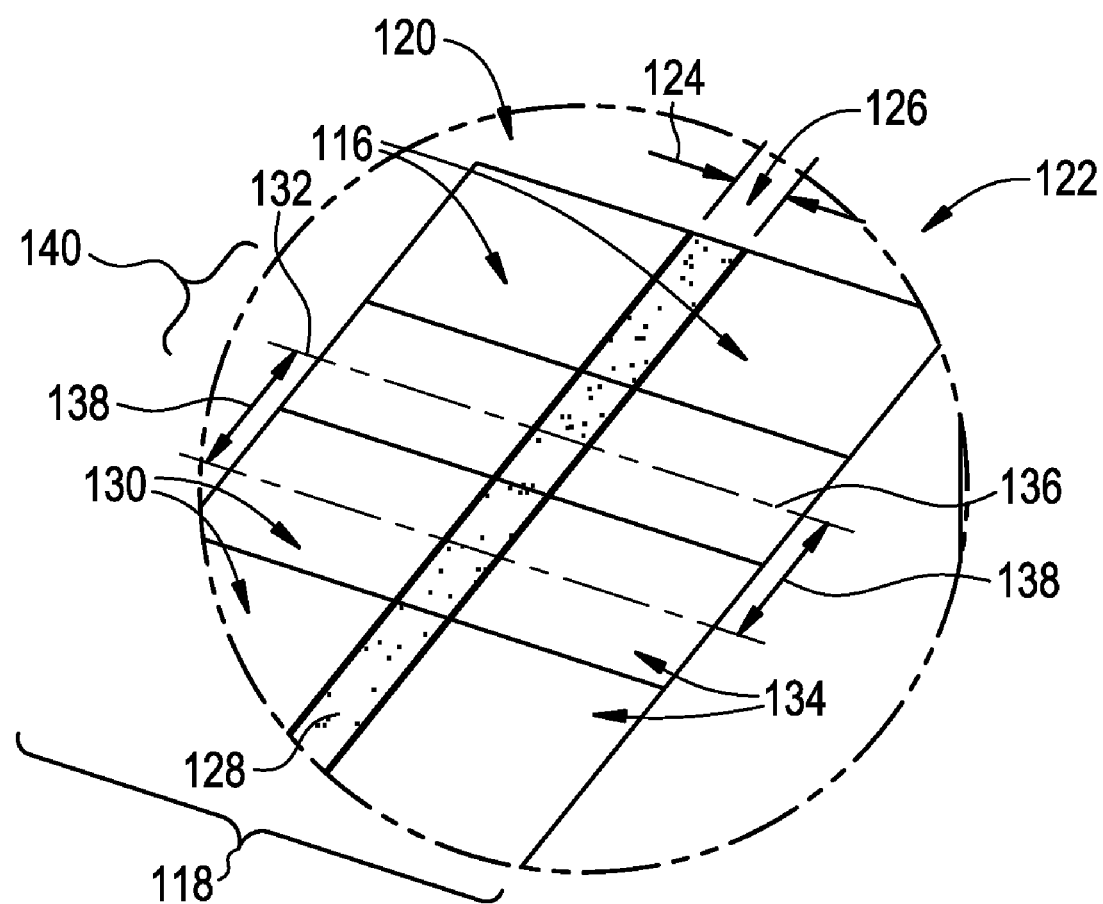
FIG. 2 is a perspective detail view of the measurement probe of FIG. 1.

Referring now to the drawings, FIGS. 1-2 illustrate an example of a measurement probe 100 in one embodiment of the present invention. The measurement probe 100 can be implemented as part of a measurement system 102, where the measurement probe 100 can be placed on a scan surface 104 of a test object 108. Exemplary objects that can be interrogated by the measurement system 102 as the test object 108 include, but are not limited to, pipes, ducts, plates, vessels, and tanks, among many others. These test objects 108 may be susceptible to corrosion such as, for example, if the test object 108 is exposed to materials that cause oxidation of an opposing surface 106 that is opposite of the scan surface 104 of the test object 108. As discussed in more detail below, the measurement system 102 may also include a test instrument 110 and a cable 112 that exchanges information, e.g., data, control instructions, etc., between the test instrument 110 and the measurement probe 100.

The probes of the type that can be used as measurement probe 100 can have a scan area 114 that has a length L. The length L can vary in a manner that permits the measurement probe 100 to measure a variety of characteristics of the test object 108. These characteristics may include, but are not limited to, the material thickness between the scan surface 104 and the opposing surface 106 of the test object 108, the material thickness between the scan surface 104 and the opposing surface 106 of the test object 108 when the opposing surface 106 is corroded, as well as other defects, anomalies, and deviations that may be located at different depths between the scan surface 104 and the opposing surface 106 of the test object 108.

This is beneficial because probes like the measurement probe 100 can be used to interrogate the test object 108 in a manner that would normally require separate devices. This includes, for example, devices that have qualities that are optimized for detecting defects that are near the scan surface 104 of the test object 108 (hereinafter, "near-distance detectability"), and devices that have qualities that are optimized for detecting defects that are located deeper in the test object 108 (hereinafter, "far-distance detectability"). It is likewise beneficial that the length L of the scan area 114 can be configured so as to substantially reduce both the time that is required to interrogate the test object 108, as well as the likelihood that defects are missed during interrogation of the test object 108. Additional details about the construction of probes that are suited for use as the measurement probe 100 are provided in connection with the embodiment of a measurement probe that is illustrated in FIGS. 3-6 below. Before continuing with that description, however, a general discussion of the components and other aspects of the measurement probe 100 and its implementation in the measurement system 102 follows immediately below.

In the present example, the scan area 114 of the measurement probe 100 may include a plurality of transducer elements 116 that can be arranged in an array 118. The array 118 can have a transmitter side 120 and a receiver side 122, which can be positioned in a spaced relationship 124 from the transmitter side 120. Here, the spaced relationship 124 forms a gap 126 that describes the minimum distance between the interior portions of the transmitter side 120 and the receiver side 122. This distance can vary. In one example, this distance can be less than about 0.5 mm, and in certain embodiments of the measurement probe 100 this distance can be from about 0 mm to about 0.75 mm. As discussed in more detail in connection with FIGS. 3-4 below, embodiments of the measurement probe 100 may also include a cross-talk barrier 128, which can be disposed in the gap 126 so as to separate the transmitter side 120 and the receiver side 122.

The transmitter side 120 may include a plurality of transmitter elements 130 that have a transmitter centerline 132, and the receiver side 122 may include a plurality of receiver elements 134 that have a receiver centerline 136. Typically the transmitter elements 130 and the receive elements 134 are spaced at a pitch 138, which in the present example is measured between the transmitter centerline 132 of adjacent transmitter elements 130, and between the receiver centerlines 136 of adjacent receiver elements 134. In one example, the pitch 138 can vary in a manner consistent with the other dimensions of the embodiments of the measurement probe 100.

The receiver elements 134 can be configured to receive echo signals from the test object 108. Exemplary echo signals include, but are not limited to, acoustic signals, and/or acoustic waves that correspond to the acoustic signals transmitted by the transmitter elements 130, and which are reflected back from the test object 108 toward the measurement probe 100. Each of the transmitter elements 130 and the receiver elements 134 can be constructed, in whole or in part, of a piezoelectric material, including, for example, piezoelectric ceramics, lead zirconate titanate, lead mataniobate, piezoelectric crystals, and any combinations thereof. In one example, one or more of the transmitter elements 130 and one or more of the receiver elements 134 may include a 1-3 type piezocomposite material.

In one embodiment of the measurement probe 100, the scan area 114 can have one or more active groups 140. Typically the active groups 140 comprise a plurality of transducer elements 116, and more particularly the active groups 140 may include one or more of the transmitter elements 130 and one or more of the receiver elements 134. By way of non-limiting example, each of the active groups 140 may have one of the transmitter elements 130 and one of the receiver elements 134, where the receiver element 134 receives the echo signals that correspond to the acoustic signals that originate from the transmitter element 130 in the active group 140. In other examples of the measurement probe 100, each of the active groups 140 may include any number of the transmitter elements 130 and the receiver elements 134.

The number of the transmitter elements 130 and the receiver elements 134 in the active groups 140 can be determined in accordance with the depth of the defect in the test object 108. Typically the depth is measured from the scan surface 104 into the test object 108. For example, the depth of defects that require the near-distance detectability may be generally less than about 5 mm. On the other hand, the depth of defects that require the far-distance detectability may be generally greater than, or equal to about 5 mm, with certain embodiments of the measurement probe 100 being configured to detect defects that are at depths of at least about 50 mm.

It is noted that the designation of "the near-distance detectability" and "the far-distance detectability" as used herein is merely used to designate the relative qualities of one embodiment of the measurement probe, e.g., the measurement probe 100. This, however, is not meant to limit the scope or spirit of the present disclosure, inasmuch as embodiments of other probes disclosed, described, and contemplated herein may have other qualities. These other qualities may be the same, different, or of slightly different variations so as to cause such qualities to be used for defects that may have depths that fall outside of the depths discussed above.

The active groups 140 that are used for the near-distance detectability may require a number of the transmitter elements 130 and a number of the receiver elements 134 that is less than the numbers that are required for the far-distance detectability. In one example, when the qualities of the measurement probe 100 are configured for the near-distance detectability, the active groups 140 may only have one of the transmitter elements 130 and one of the receiver elements 134. In another example, when the qualities of the measurement probe 100 are configured for the far-distance detectability, the active groups 140 may have at least seven of the transmitter elements 130 and at least seven of the receiver elements 134.

Discussing the test instrument 110 in more detail, the test instrument 110 that can be used in the present embodiment of the measurement probe 100 of FIGS. 1-2 can be configured to operate the measurement probe 100 so as to activate, and collect data from, the scan area 114. This includes, for example, being configured to activate particular ones of the active groups 140 of the scan area 114, and being configured to activate particular ones of the transmitter elements 130 and the receiver elements 134. Exemplary devices that are suited for use as the test instrument 110 can include, but are not limited to, computers (e.g., desktop computers, laptop computers, etc.), ultrasound instruments, ultrasound systems, and the like. An example of an ultrasound instrument is the Phasor XS Phased Array Ultrasound Instrument available from GE Inspection Technologies of Lewiston, Pa.

By way of non-limiting example, and as it is illustrated in FIGS. 1-2, the test instrument 110 can include an interface 142 that has a display 143 that displays information, e.g., data information, images, etc., which can be collected by the measurement probe 100. The interface 142 can also include one or more controls 144 that control the operation of the measurement probe 100. In one embodiment of the measurement probe 100, the controls 144 can be configured to select the length L of the scan area 114, the number of active groups 140 in the scan area 114, and/or the number of the transmitter elements 130 and the receiver elements 134 in each of the active groups 140.

In view of the foregoing, and discussing one implementation of the measurement probe 100 and the measurement system 102 in more detail, a user, e.g., a field engineer, can position the measurement probe 100 on the scan surface 104 of the test object 108 so that the acoustic signals from the transmitter elements 130 can enter the test object 108. The field engineer can move the probe 100 along the scan surface 104, e.g., in a direction 146 that may be substantially perpendicular to the scan area 114. This may cause the scan area 114 to come into contact with the area of interest of the test object 108. The term "area of interest" is used herein to describe the portion of the test object 108 where data is to be collected with the measurement system 102. An area of interest, for example, may include the test object 108 in its entirety, and/or a portion of the test object 108. The area of interest may also include portions of the test object 108 that are corroded, and/or portions of the test object where defects are found. The area of interest may further include the scan surface 104 of the test object 108 in its entirety, and/or a portion of the scan surface 104 of the test object 108.

In one embodiment of the measurement probe 100, the field engineer can adjust the controls 144 of the test instrument 110 so as to accommodate changes in the physical characteristics of the area of interest of the test object 108. This includes changes in the thickness of the material between the scan surface 104 and the opposing surface 106 of the test object 108. For example, certain portions of the test object 108 may be corroded so that the material thickness of one portion of the test object 108 is different than the material thickness of another portion of the test object 108. The physical characteristics also include the depth of the defect from the scan surface 104. For example, one defect may have a depth within the test object 108 that is different from other defects within the test object 108, which are also detected with the measurement system 102.

To accommodate for the difference in the physical characteristics of the area of interest, the field engineer can adjust the controls 144 to modify one or more parameters of the ultrasound beam that is generated by the measurement probe 100. For example, the ultrasound beam may have a near-field parameter for near-field detectability and a far-field parameter for far-field detectability. These may be different based on the number of the transmitter elements 130 and the number of the receiver elements 134 that are utilized in the active groups 140. In another example, the near-field parameter may be different from the far-field parameter based on the number of active groups 140 that are found in the scan area 114. In still another example, each of the near-field parameter and the far-field parameter can correspond to different depths inside of the test object 108.

Figure 3:
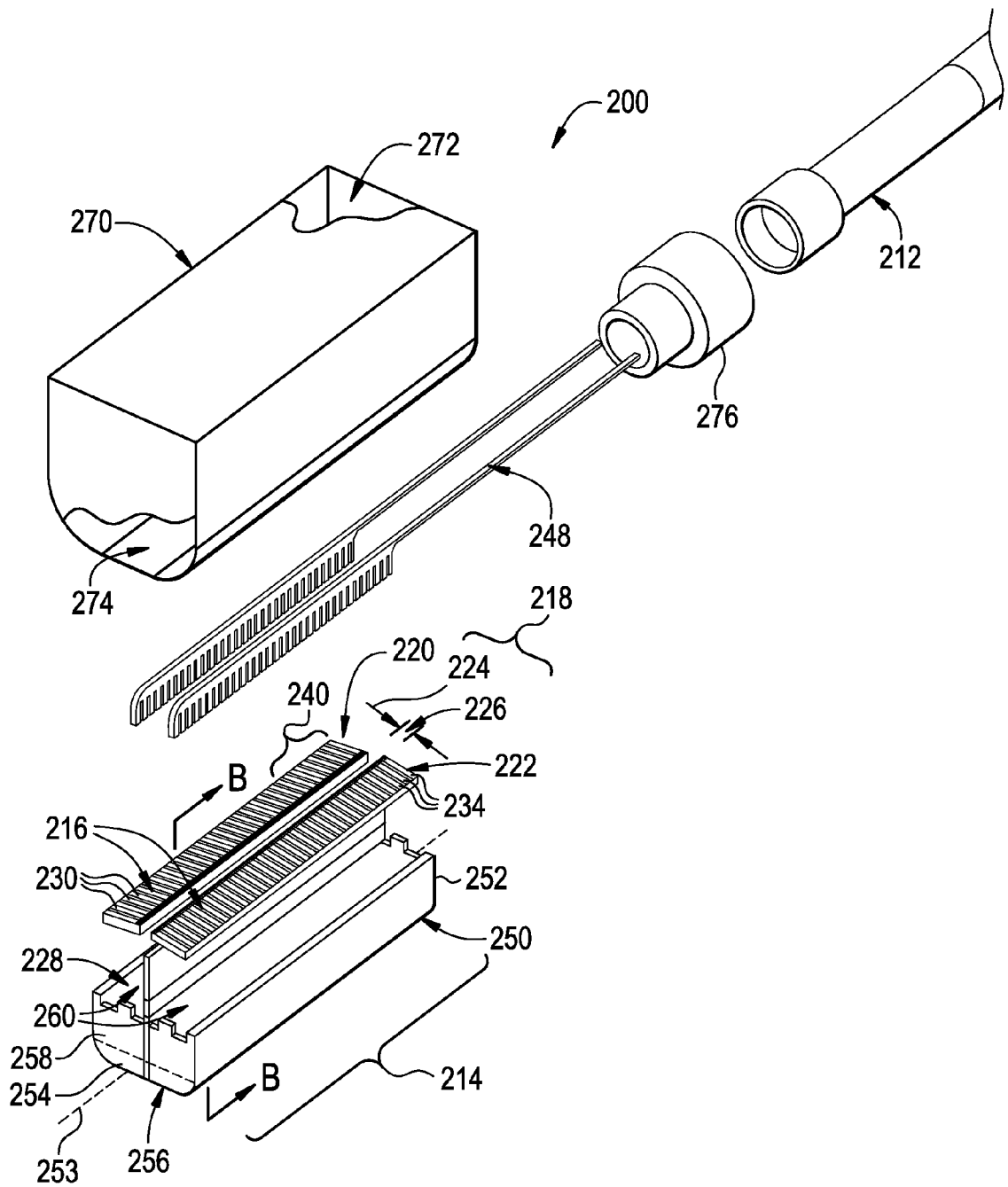
FIG. 3 is a perspective view of another embodiment of a measurement probe.
Figure 4:
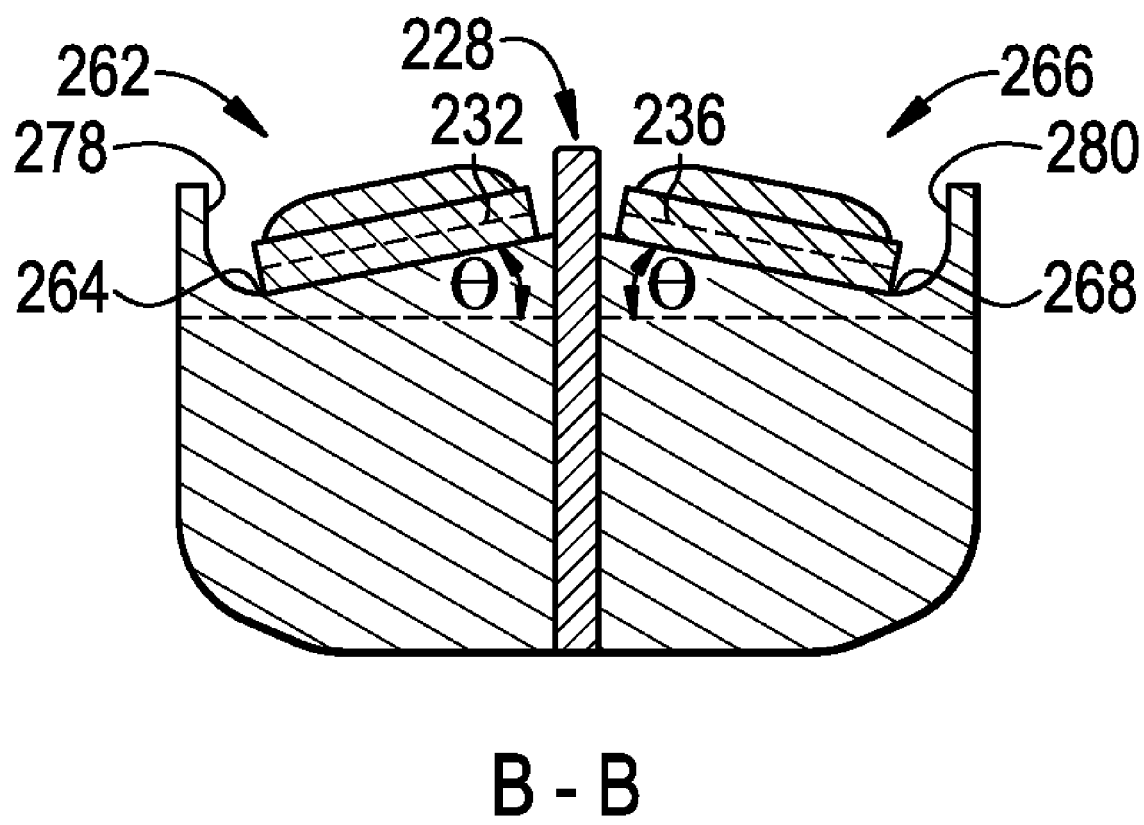
FIG. 4 is a side cross-section view of the measurement probe of FIG. 3.

Referring next to FIGS. 3-4, and also to FIGS. 1-2, another example of a measurement probe 200 is illustrated, where portions of the measurement system, e.g., system 102 (FIG. 1), have been removed for clarity. It is noted that, where applicable, numerals are used to designate like components, such as those components in FIGS. 1-2 above, but that the numerals are increased by 100. For example, the measurement probe 200 of FIGS. 3-4 can include a scan area 214, transducer elements 216 that can be arranged in an array 218, and more particularly, in a transmitter side 220 and a receiver side 222 that can be separated by a cross-talk barrier 228. In the present example, each of the transmitter side 220 and the receiver side 222 can include, respectively, a plurality of transmitter elements 230 and a plurality of receiver elements 234.

The measurement probe 200 can also include a wiring harness 248, and a delay block 250. The delay block 250 can have a body 252 that has a longitudinal axis 253, a lower portion 254 that has a scan surface 256, and an upper portion 258 that has a pair of recessed areas 260. The recessed areas 260 can include a transmitter recessed area 262 that has a transmitter support surface 264, and a receiver recessed area 266 that has a receiver support surface 268. Embodiments of the measurement probe 200 may also include a housing 270 that has an interior cavity 272 with a bottom opening 274 that may be sized and configured to receive the body 252 so that at least the upper portion 258 of the delay block 250, the wiring harness 248, as well as the transducer elements 216 are surrounded by the housing 270.

A connective element 276 can also be provided and disposed, e.g., on one or more of the body 252 and the housing 270. Connective elements of the type used as the connective element 276 may typically include devices for coupling the cable 112 (FIG. 1) to the measurement probe 200. This may include, for example, screw-threaded fittings, snap fittings, pressure release fittings, deformable fittings, quick-release fittings, and any combinations thereof. In one example, the connective element 276 can be adapted to mate with threaded connectors that are on the cable 112 (FIG. 1).

By way of non-limiting example, the body 252 of the delay block 250 can acoustically couple, via the scan surface 256, the transducer elements 216 to the surface 104 (FIG. 1) of the test object 108 (FIG. 1). The body 252 can be constructed monolithically, or in a number of parts that are assembled together to form the delay block 250. For example, the lower portion 254 that includes the scan surface 256 may be detachable from the body 252 so that the scan surface 256 can be removed and/or replaced on the body 252. For example, it is contemplated that the scan surface 256 can be removed and replaced, either in whole or in part, when the scan surface 256 is worn, damaged, or otherwise modified in a manner that limits the capabilities of the measurement probe 100.

Materials that are used for the body 252 are generally selected based on their acoustic velocity, or the velocity of the particles in the material as the material transmits an acoustic wave. Typically the acoustic velocity of the materials in the body 252 can be different from the acoustic velocity of the materials of the test object 108 (FIG. 1). Exemplary materials include, but are not limited to, metals and plastics, and in one embodiment of the measurement probe 200 the materials may include one or more of plexi-glass and/or poly-styrene.

As it is seen in the example of FIG. 3, and more particularly in the section view of FIG. 4 where the measurement probe 200 is shown in one example of its assembled form, the recessed areas 260 can be located near the upper portion 258 of the body 252 so that, when the measurement probe 200 is constructed, the transmitter side 220 and the receiver side 222 are placed into the recessed areas 260. Each of the transmitter support surface 264 and the receiver support surface 268 may be angled, or canted, away from the cross-talk barrier 228. A roof-angle θ that is measured with respect to scan surface 256 may define the angle of the transmitter support surface 264 and/or the receiver support surface 268. Values of the roof-angle θ can be less than about 10°, with the roof-angle θ in certain constructions of the measurement probe 200 being from about 3° to about 7°. It is also contemplated, and illustrated in the example of the measurement probe 300 of FIGS. 5-6, that the value of the roof-angle θ can be about 0°.

The transmitter recessed area 262 can include at least one transmitter internal surface 278, and the receiver recessed area 266 can include at least one receiver internal surface 280. The internal surfaces 278, 280 may bound the respective recessed area 260 in a manner that creates internal dimensions relative to, and measured from, the other internal surfaces 278, 280 of the recessed areas 260. The internal dimensions can be sized in a manner that permits the transmitter recessed area 262 and the receiver recessed area 266 to receive, respectively, the transmitter side 220 and the receiver side 222. In one example, the internal dimensions can be selected so that the transducer elements 216 are supported by the support surfaces 264, 268.

The internal surfaces 278 of the transmitter recessed area 262 can also be constructed and dimensioned with respect to the internal surfaces 280 of the receiver recessed area 266 so that the transmitter elements 230 are substantially aligned with the receiver elements 234 when the transmitter side 220 and the receiver side 222 are in the recessed areas 260. It is to be understood, however, that the term "substantially aligned" as used and described herein takes into consideration certain manufacturing tolerances, assembly tolerances, and other deviations that can be injected into the overall assembly of the measurement probe 200. Such tolerances and deviations may, for example, cause one or more of the transmitter element 230 and the receiver elements 234 to be so located that all of the transmitter elements 230 are not perfectly aligned with all of the receiver elements 234.

The term "substantially aligned" may also be considered in the relative when used as the description of the position of the transmitter array, the receiver array, the transmitter elements, and/or the receiver elements to be so dimensioned within certain tolerances, or, in the alternative, as the description of the position that causes the alignment of individual ones of the transmitter elements and the receiver elements to remain within certain tolerances. For example, regarding the former description it is contemplated that the dimensions of the recessed area will be within a desired tolerance, e.g., about ±0.5 mm. On the other hand, regarding the latter description it is contemplated that the position of the transmitter elements in relations to the receiver elements in probes that are made in accordance with the concepts disclosed herein will be consistent with a desired value, e.g., the nominal deviation between co-planar surfaces of the transmitter element and the receiver element, and/or the nominal deviation between co-axially aligned centerlines of the transmitter element and the receiver element.

The cross-talk barrier 228 can be constructed in a manner that acoustically and/or mechanically isolates the transmitter side 220 and the receiver side 222. This includes, for example, being constructed so as to prevent acoustic waves and electromagnetic energy from being communicated between the transmitter elements 230 and the receiver elements 234. As it is illustrated in FIGS. 3-4, the cross-talk barrier 228 can extend into the body 252, and in one construction of the measurement probe 200 the cross-talk barrier 228 extends to the scan surface 256. It can include materials such as, for example, copper foil, closed-cell polymer foam, cork-filled rubber, and any combinations thereof.

Exemplary materials for use in the housing 270 include, but are not limited to, metals (e.g., aluminum, steel, brass, etc.), and composites, among many others. Likewise, manufacturing processes implemented to make the components of the probe 200 include casting, molding, extruding, machining (e.g., turning, and milling) and other techniques that are suitable for forming the various pieces and components of the probe 200, and more particularly, the body 252 of the delay block 250, and the housing 270, each of which is disclosed and described herein. Because these processes, and the materials that are utilized by such processes, are generally well-known to those having ordinary skill in the art, no additional details will be provided herein, unless such details are necessary to explain the embodiments and concepts of the present invention.

Figure 5:
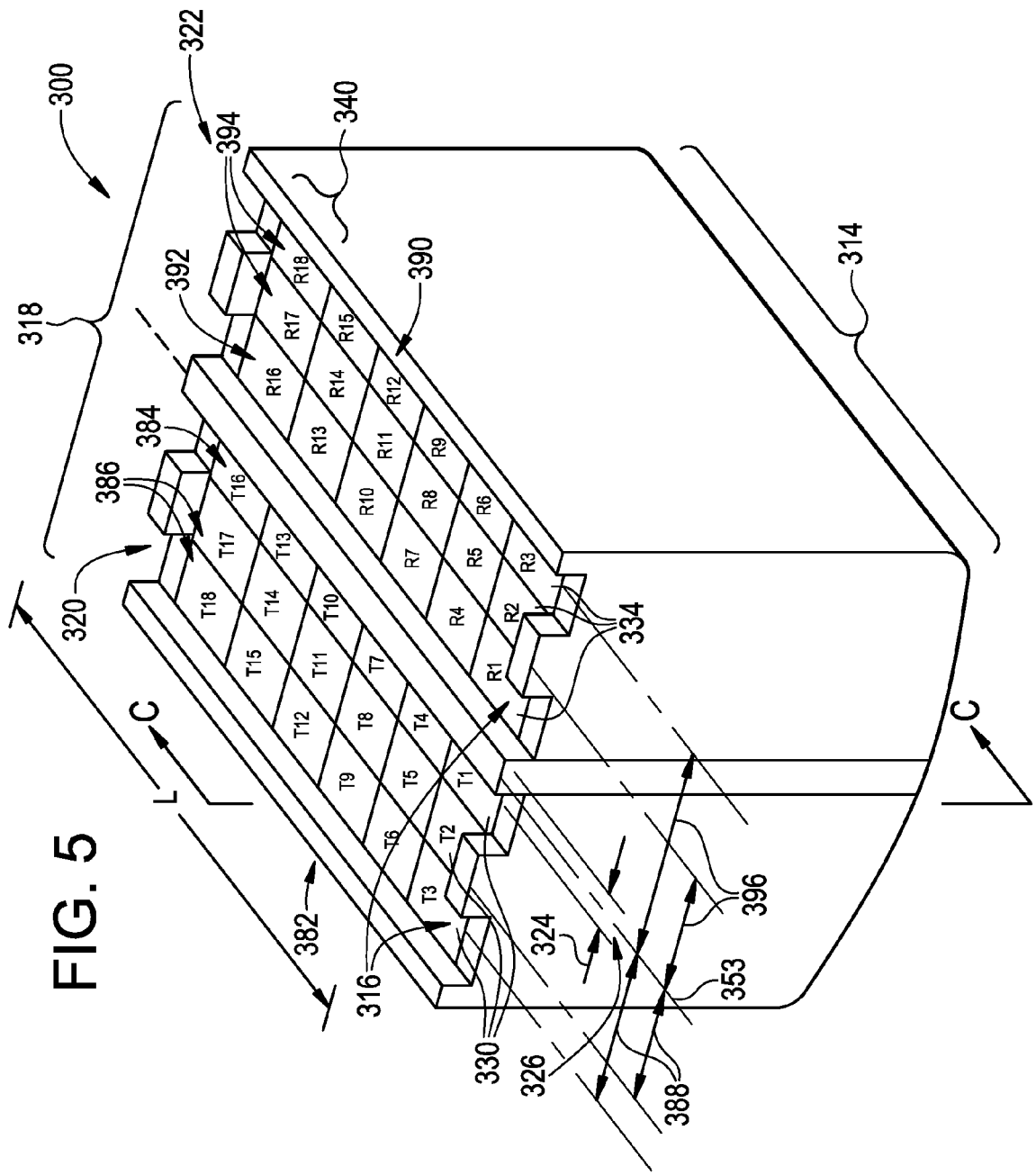
FIG. 5 is a perspective view of still another embodiment of a measurement probe.
Figure 6:
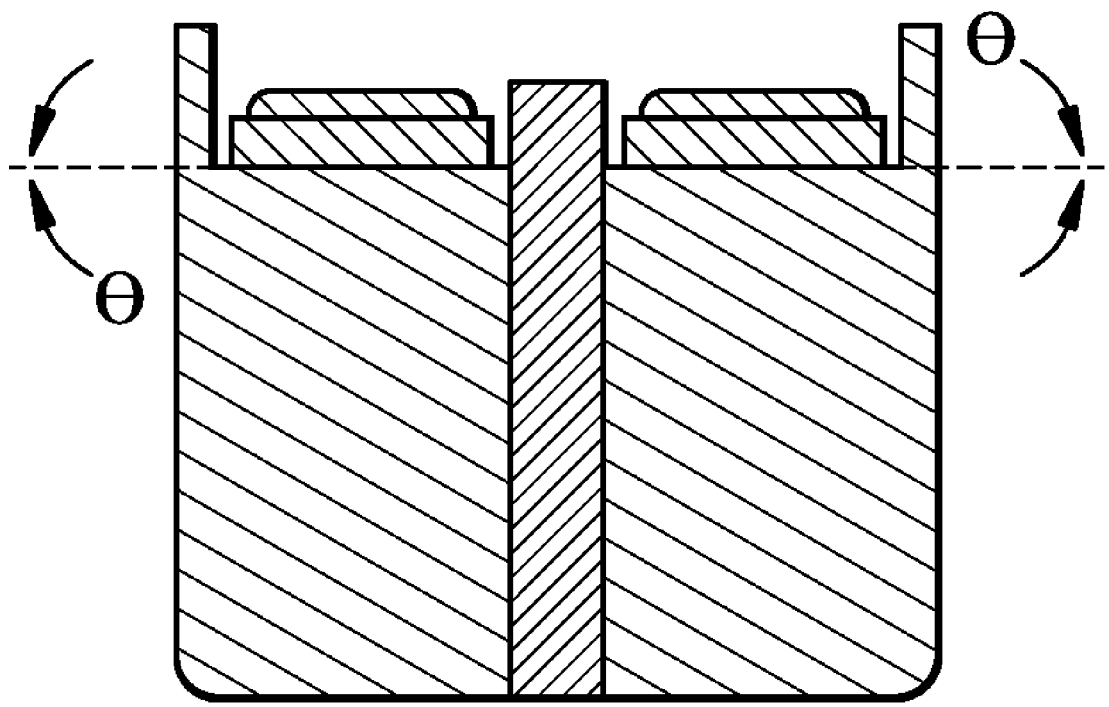
FIG. 6 is a side cross-section view of the measurement probe of FIG. 5.

Still another example of a measurement probe 300 is illustrated in FIGS. 5-6. Here, as with the example of the measurement probe 200 of FIGS. 3-4, like numerals are used to designate like components in the measurement probe 300, but that the numerals in FIGS. 5-6 are increased by 100. For example, it is seen in FIGS. 5-6 that the measurement probe 300 can include a scan area 314 with a length L, transducer elements 316 that can be arranged in an array 318, and more particularly in a transmitter side 320 and a receiver side 322 that can be separated by a cross-talk barrier 328.

As mentioned in connection with the discussion of FIGS. 1-2 above, the transmitter side and the receiver side in embodiments of the measurement probes disclosed herein can each include, respectively, a plurality of transmitter elements 330 and a plurality of receiver elements 334. In the present example of FIG. 5-6, it is seen that the transmitter elements 330 (labeled T1-T18) are arranged in a transmitter grid 382. More particularly, each of the active groups 340 can include an inner transmitter element 384 proximate the gap 326, and at least one outer transmitter element 386 that is located an outer distance 388 that is measured from the longitudinal axis 353. The receiver elements 334 (labeled R1-R18) are likewise arranged in a receiver grid 390 so that each of the active groups 340 includes an inner receiver element 392 that is separated from the inner transmitter element 384 by the spaced relationship 324. The active group 340 also includes at least one outer receiver element 394 that is located an outer distance 396 from the longitudinal axis 353.

When the measurement probe 300 is implemented in a system, such as the system 102 of FIG. 1, each of the transducer elements 316 that are found in the transmitter grid 382 and the receiver grid 390 can be operated individually. In one example, the transmitter element T1 can be activated to transmit the ultrasound beam, and the receiver element R1 can be activated to receive the echo signal that corresponds to that ultrasound beam. In another example, the transmitter elements T1-T6 can be activated so as to transmit ultrasound beams, and the receiver elements R1-R6 can be activated to receive the echo signal that correspond to those ultrasound beams. Nevertheless, the combinations of the transmitter elements 330 and the receiver elements 334 that are activated are limited only by the number of the transducer elements 316 that are found in the transmitter grid 382 and the receiver grid 390.

Embodiments of the measurement probe 300 are also configured so that certain ones of the transducer elements 316 can undergo controlled-excitation so as to manipulate the parameters of the ultrasound beam that is directed into the test object, e.g., test object 108 (FIG. 1). These parameters include, but are not limited to, the direction, the angle, the focal distance, and the focal spot size of the ultrasound beam. These terms are generally recognized by those artisans having ordinary skill in the art, and so these terms will not be defined or described herein, but rather referred to in context of the concepts of the embodiment of the measurement probes disclosed and contemplated in the present disclosure. For example, and by way of non-limiting example, it is contemplated that the direction of the ultrasound beam can be manipulated by varying the time at which each of the transmitter elements 330 is excited with respect to the other transmitter elements in the transmitter grid 382.

Other embodiments of the measurement probe 300 are further configured so that the transducer elements 316 can undergo controlled-excitation so that the measurement probe 300 exhibits certain operational characteristics that are consistent with the characteristics of phased array ultrasonic technology. One exemplary operational characteristic includes being configured to excite one or more of the transmitter elements 330 so as to generate the ultrasound beam in accordance with certain beam-scanning patterns, such as, for example, electronic scanning, dynamic depth focusing, and azimuthal scanning. By way of non-limiting example, it is contemplated that the embodiments of the measurement probe 300 can have operational characteristics that are consistent with "1.25D," "1.5D," "1.75D," and "2D" transducer arrays. Again, as discussed in connection with the parameters of the ultrasound beam immediately above, the control structure, instrumentation, and other considerations that are required to achieve such patterns will be recognized by those artisans familiar with phased array ultrasonic technology, and so will not be discussed herein. However, for purposes of example only, as used herein, the "1.25D" transducer provides a variable elevation aperture, with static focusing; the "1.5D" transducer array provides a variable elevation aperture, shading, and focusing that is symmetric about the centerline of the array; the "1.75D" transducer array provides variable elevation aperture, shading, and focusing that is not symmetric about the centerline of the array; and the "2D" transducer array provides full electronic focusing and steering.

Figure 7:
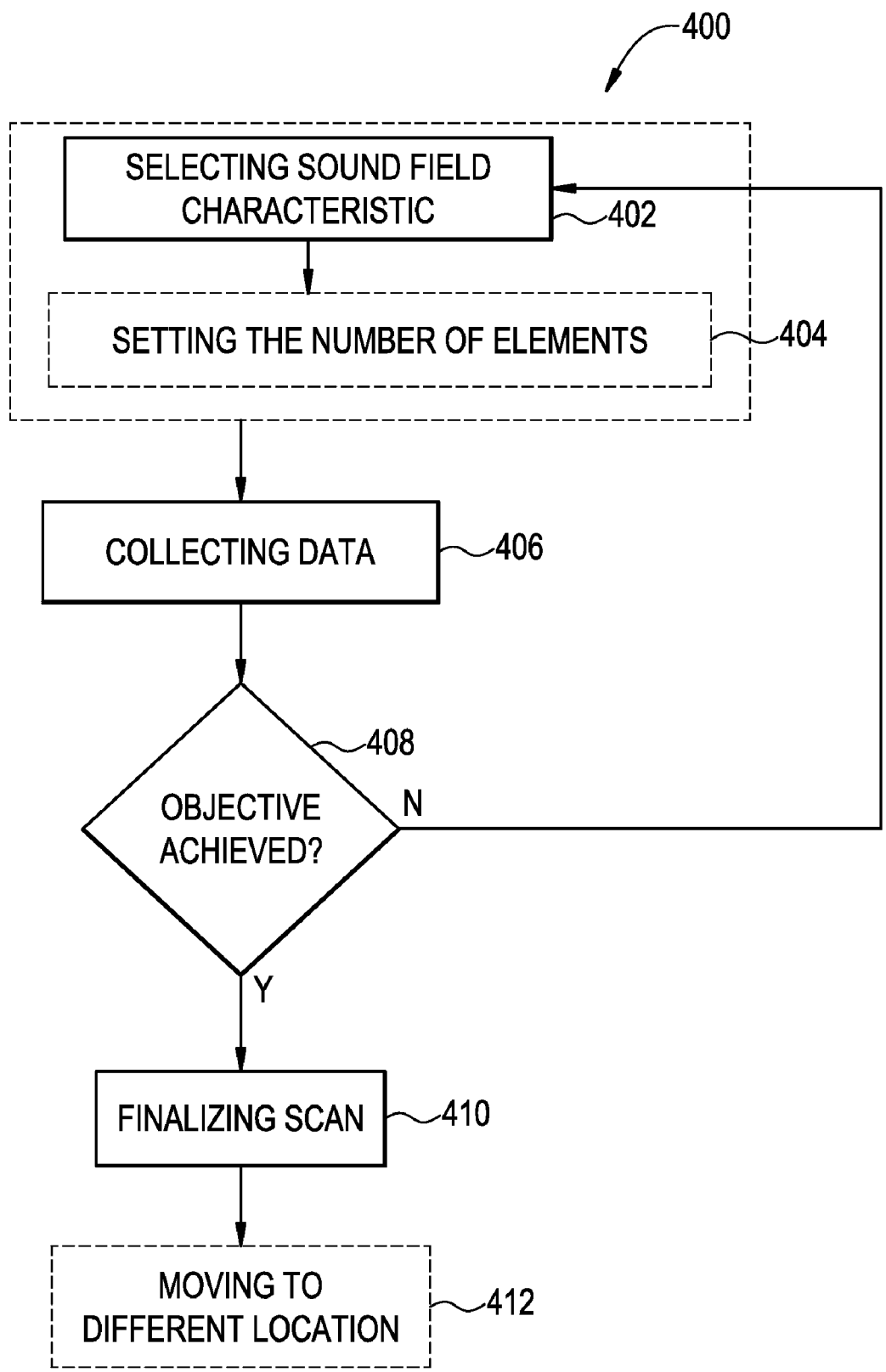
FIG. 7 is a flow diagram of a method of implementing a measurement system that includes a measurement probe, such as the measurement probes in FIGS. 1-6.

Discussing the operation of measurement probes that are made in accordance with one or more embodiments of the present invention, FIG. 7 illustrates a method 400 for measuring the thickness of a test object using the measurement probe, e.g., measurement probes 100, 200, 300 (collectively, "the probe"). Here, the method 400 may include, at step 402, selecting a parameter, e.g., a first parameter, for the ultrasound beam. This may include, for example, at step 404 setting the number of transmitter elements and the number of receiver elements for the active groups of the scan area. Then, the method 400 may include, at step 406, collecting data by interrogating the surface of the test object with the probe. Generally, this can be accomplished by placing the scan surface of the probe against the surface of the test object, and then moving the probe across the surface in a direction that is substantially perpendicular to the scan area. This may be repeated any number of times if the entire surface of the test object is to be scanned, or it can be repeated only as necessary based on the size of the area of interest of the test object.

After interrogating the inner volume of the test object, or alternatively after interrogating only a portion of the inner volume, the method 400 next may include, at step 408, determining if the parameter achieved the objectives of the test. This can include evaluating the information that is displayed by the test instrument including, for example, examining the resolution of an image of the test object on the test instrument, and/or comparing the image to a known good image that has the resolution that is desired. If the resolution is adequate to meet the objectives of the test, then the method may include at step 410 finalizing the scan of the test object, and, at step 412, moving to a different location on the surface of the test object.

If the resolution is not adequate, then the method can return to step 402, selecting a parameter for the ultrasound beam, and another parameter, e.g., a second parameter, is selected by, e.g., changing the number of the transmitter elements and the number of the receiver elements for the active groups of the scan area. In the present example, the probe is used to scan the surface using the second sound field characteristic, and it is determined if the second sound field characteristics achieve the objective of the test. If the resolution is not adequate, then the method 400 can continue, e.g., in accordance with steps 402-408, until the resolution meets the objectives of the test. Then, as discussed above, the method 400 may include at step 410 finalizing the scan of the test object, and at step 412, moving to a different location on the surface of the test object.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A measurement system, comprising:
   a measurement probe including a delay block having a longitudinal axis and a plurality of transducer elements acoustically coupled to the delay in a manner forming an active group, the active group including a transmitter side for generating an ultrasound beam and a receiver side for receiving an echo signal, the receiver side in a spaced relationship with the transmitter side, the spaced relationship forming a gap about the longitudinal axis, the gap including a cross-talk barrier disposed in a manner acoustically separating the transmitter side and the receiver side; and
   a test instrument coupled to the measurement probe, the test instrument including an interface controlling at least one transducer element in the active group in a manner causing a first parameter of the ultrasound beam,
   wherein the receiver side includes at least one transducer element responsive to the echo that corresponds to the ultrasound beam, and
   wherein the measurement probe includes a first active group and a second active group that has a number of transducer elements that is different from the first active group.

2. The measurement system according to claim 1, wherein the number of transducer elements is selected in accordance with the first parameter of the ultrasound beam.

3. The measurement system according to claim 1, wherein each of the receiver side and the transmitter side includes a plurality of the transducer elements.

4. The measurement probe according to claim 3, wherein the transducer elements include an inner transducer element located a first distance from the longitudinal axis, and at least one outer transducer element located a second distance from the longitudinal axis that is greater than the first distance, the first distance and second distance measured substantially perpendicular to the longitudinal axis.

5. The measurement probe according to claim 1, wherein the spaced relationship is less than about 3 mm.

* * * * *